(12) United States Patent
Peukert et al.

(10) Patent No.: US 9,956,018 B2
(45) Date of Patent: May 1, 2018

(54) BONE SCREW

(71) Applicant: AESCULAP AG, Tuttlingen (DE)

(72) Inventors: Andrea Peukert, Tuttlingen (DE); Sven Krüger, Trossingen (DE); Michael Rauschmann, Frankfurt am Main (DE); Bronek Boszczyk, Wollaton (GB)

(73) Assignee: Aesculap AG (DE)

(*) Notice: Subject to any disclaimer, the term of this patent is extended or adjusted under 35 U.S.C. 154(b) by 0 days. days.

(21) Appl. No.: 14/902,632

(22) PCT Filed: Jul. 7, 2014

(86) PCT No.: PCT/EP2014/064464
§ 371 (c)(1),
(2) Date: Jan. 4, 2016

(87) PCT Pub. No.: WO2015/004063
PCT Pub. Date: Jan. 15, 2015

(65) Prior Publication Data
US 2016/0166300 A1    Jun. 16, 2016

(30) Foreign Application Priority Data

Jul. 8, 2013 (DE) .......... 10 2013 107 170

(51) Int. Cl.
A61B 17/86 (2006.01)
A61B 17/70 (2006.01)

(52) U.S. Cl.
CPC ........ A61B 17/863 (2013.01); A61B 17/7032 (2013.01)

(58) Field of Classification Search
CPC ............ A61B 17/7032; A61B 17/8625; A61B 17/863
See application file for complete search history.

(56) References Cited

U.S. PATENT DOCUMENTS 3,466,748 A     9/1969  Christensen
5,259,398 A  * 11/1993  Vrespa ................. A61B 17/863
                                                    128/898
5,891,146 A  *  4/1999  Simon .................. A61B 17/863
                                                    411/414
(Continued)

FOREIGN PATENT DOCUMENTS

DE    102008019489    11/2009
DE    202012009023     1/2013
(Continued)

OTHER PUBLICATIONS

German Search Report for German Application No. 10 2013 107 170.8 dated Feb. 11, 2014, with partial translation.
(Continued)

Primary Examiner — Julianna N Harvey
(74) Attorney, Agent, or Firm — RatnerPrestia

(57) ABSTRACT

A bone screw includes a screw shaft with an external thread. The screw shaft anchors the bone screw in a bone. A proximal end of the screw shaft includes a screw head. The ratio between the outer thread diameter and the thread core diameter increases toward the screw head in a proximal screw shaft portion or in the area of the thread's run-out.

6 Claims, 7 Drawing Sheets

(56) References Cited

U.S. PATENT DOCUMENTS

| | | | | |
|---|---|---|---|---|
| 6,030,162 | A * | 2/2000 | Huebner | A61B 17/1682 |
| | | | | 411/263 |
| 6,264,677 | B1 * | 7/2001 | Simon | A61B 17/0401 |
| | | | | 411/414 |
| 2002/0016594 | A1 * | 2/2002 | Schlapfer | A61B 17/863 |
| | | | | 606/308 |
| 2010/0094352 | A1 * | 4/2010 | Iott | A61B 17/8605 |
| | | | | 606/301 |
| 2011/0172718 | A1 | 7/2011 | Felix | |
| 2011/0313473 | A1 * | 12/2011 | Prandi | A61B 17/863 |
| | | | | 606/315 |
| 2012/0215263 | A1 * | 8/2012 | Lee | A61B 17/7037 |
| | | | | 606/305 |
| 2012/0232600 | A1 | 9/2012 | Wen | |
| 2013/0331947 | A1 * | 12/2013 | Surma | A61B 17/1739 |
| | | | | 623/21.12 |

FOREIGN PATENT DOCUMENTS

| | | |
|---|---|---|
| WO | 0032125 | 6/2000 |
| WO | 2005020831 | 3/2005 |
| WO | 2012103354 | 8/2012 |

OTHER PUBLICATIONS

International Search Report for International Application No. PCT/EP2014/064464 dated Oct. 20, 2014.
PCT Written Opinion Containing Cited References for PCT/EP2014/064464 dated Oct. 20, 2014.

* cited by examiner

US 9,956,018 B2

BONE SCREW

RELATED APPLICATIONS

This application is the U.S. National Phase of International Application No. PCT/EP2014/064464, filed Jul. 7, 2014 and claiming the benefit of priority of German Application No. DE 10 2013 107 170.8, filed Jul. 8, 2013. The contents of International Application No. PCT/EP2014/064464 and German Application No. DE 10 2013 107 170.8 are incorporated by reference herein in their entireties.

FIELD

The present invention relates to a bone screw, in particular a pedicle screw.

BACKGROUND

Pedicle screws usually serve for the dorsal stabilization of the spinal column in the event of fractures, tumors, inflammations, deformities and degeneratively induced instabilities by means of a transpedicular screw connection. In doing so, pedicle screws are placed in the pedicles of neighboring vertebrae, creating an angularly stable connection between the pedicle screws arranged axially one above the other and an axially extending longitudinal member or bar. In such an arrangement, the pedicle screws and the longitudinal member constitute a vertebral stabilization system.

The pedicle screws are screwed through the pedicle into the vertebral body (corpus vertebrae) between the transverse process (processus transversus) and the spinous process (processus spinosus). To this end, a pedicle screw usually comprises a screw head and an elongated screw shaft provided with an external thread. Whereas the screw head is formed like a tulip for the fixation of the longitudinal member or carries a so-called tulip, the screw shaft serves for anchoring the pedicle screw in the vertebra.

Various geometries are known with regard to the design of the screw shaft.

By way of example, screws are used which have a cylindrical thread and in which both the core diameter and the outer or flank diameter remain constant over the entire longitudinal extension of the screw shaft (cf. FIG. 4A). These screws have a very high pull-out strength which is hardly affected even in the event of turning back the screw in order to correct the position of the screw head, for instance. It is a disadvantage of constant external diameters and core diameters that the thread—which is cut into the bone by the external thread in the entry area between the transverse process and the spinous process—may wear out in case of further driving in the screw, possibly reducing the support in the area of the proximal shaft portion. A further disadvantage lies in the fact that a cylindrical thread, in particular a constant core diameter, is not capable of compacting the cancellous bone material, which is present in the vertebra, between the thread flanks.

Further, it is also known that there are screws comprising a fully conical thread in which both the outer thread diameter and the core diameter uniformly increase from the screw tip up to the screw head. The advantage of this screw geometry is to see in the fact that they have a good grip in the bone and even the proximal shaft portion cuts further into the bone; in this way, a good support is also ensured in the proximal area. However, screws comprising a fully conical thread do not allow for their subsequent fine adjustment, as otherwise the contact of the thread flanks of the screw with the bone's thread which has been excessively widened beforehand in radial direction would get lost over the entire length even in the case of only slightly turning back the screw.

This is why screws comprising a partially conical thread are frequently used, in which the core is conical and the thread is formed to be cylindrical (cf. FIG. 7A). The cylindrical thread ensures a high pull-out strength. Due to the increasingly larger core diameter, a radial pressure on the cancellous bone material is produced between the thread flanks and said bone material is compacted, improving the support. What is more, a screw comprising a partially conical thread also has a higher fatigue strength than a screw with a constant core diameter which is due to the increasing core diameter.

In the case of screws comprising a partially conical thread, however, the thread flanks become increasingly broad and dull toward the screw head; this is why said flanks do not have a cutting effect any more in the proximal area of the screw shaft, but are pressed into the thread turn in radial and axial directions and possibly expand or even burst the thread turn in the proximal area. Also in this case, a slight backward turn may result in the screw becoming loose, as the thread flanks lose the contact with the thread turn (which is expanded in axial direction).

As each of these geometries has advantages and disadvantages, combinations of these geometries are also known, such as e.g. a screw comprising a cylindrical external diameter and a core with alternating cylindrical and conical core diameter portions (cf. FIGS. 5A and 6A).

As already mentioned above, the entry point of a pedicle screw is situated between the transverse process and the spinous process, then extends through the pedicle in the axial direction of the relatively narrow pedicle and opens out into the vertebral body. In the area of the vertebral body and in the area between the entry point and the pedicle, there mainly is soft cancellous bone material, whereas dense cortical bone material can be found in the slim area of the pedicle immediately in the area of the entry point. None of the thread shapes known hitherto satisfies this bone structure of a vertebra and the inhomogenous bone strength.

SUMMARY

It is therefore the object of the present invention to provide a bone screw, in particular a pedicle screw, which ensures an optimum support if it is anchored in a bone comprising a cortical bone shell and a cancellous bone core.

A bone screw according to the invention, in particular a pedicle screw, comprises a screw shaft and a screw head provided on the proximal end of the screw shaft. The screw shaft is provided at least in portions with a one- or multi-start, self-tapping external thread for anchoring the bone screw in the bone. In this arrangement, the ratio between the outer thread diameter and the thread core diameter in a proximal screw shaft portion or in the area of the thread's run-out increases toward the screw head.

This means that the thread turns become deeper in the area of the thread's run-out and cut into the bone material even deeper. Toward the screw head, the thread becomes even "more aggressive" and has a very good grip performance in particular even for the last turn.

It is in particular the proximal thread portion or the thread's run-out which is situated in the area where the screw enters the bone, i.e. in the area of the dense cortical shell. An improved anchoring of the screw in the bone is made possible by the sharp thread flanks cutting deeper and deeper into said cortical bone material.

The design, according to the invention, of the thread's run-out may be applied inter alia to a pedicle screw, as the proximal screw shaft portion of a pedicle screw—in contrast to the middle and distal screw shaft portions—is not limited by the dimensions of the fairly slim pedicle. There is more space available in the area between the entry point and the pedicle, so that the ratio between the outer thread diameter and the thread core diameter can be increased in this area in order to achieve the advantages mentioned above.

According to one aspect of the invention, both the outer thread diameter and the thread core diameter increase in the proximal screw shaft portion and in the area of the thread's run-out, with the outer thread diameter increasing to a proportionally higher degree.

The increase of the core diameter results in that the screw exerts a radial pressure onto the bone material between the thread flanks which is mainly cancellous in the area between the entry point and the pedicle and compacts it, so that the screw experiences a superior fixation in the bone material not only by means of the thread flanks (in a form-locking manner), but also via said radial pressure (in a force-fitting manner).

The larger core diameter also enhances the fatigue strength of the screw.

Due to the fact that the ratio between the outer thread diameter and the thread core diameter increases toward the screw head, it is ensured that even the last turns of the thread keep their sharp and cutting condition despite the increasing core diameter and do not become broad and dull as is the case in the partially conical thread described above in the prior art.

Hence, the geometry according to the invention combines the advantages of a cylindrical thread's run-out with the advantages of a partially conical thread's run-out, i.e. the thread flanks which are sharp as far as to the last thread turn cut into the cortical bone shell and provide for an improved anchoring, on the one hand, and on the other hand the (cancellous) bone material is compacted by the increasing core diameter during driving in the screw.

According to one aspect of the invention, the thread core diameter is cylindrical and constant in the proximal screw shaft portion, whereas the outer thread diameter increases in said portion, which is why the ratio between the outer thread diameter and the thread core diameter increases toward the screw head.

According to one aspect of the invention, both the outer thread diameter and the thread core diameter linearly increase in the proximal screw shaft portion. In other words, both the outer thread diameter and the thread core diameter increase in conical manner. On the one hand, this geometry can be manufactured easier, and on the other hand the proximal thread portion can be driven into the bone with an unchanging torque.

According to one aspect of the invention, both the outer thread diameter and the thread core diameter exponentially increase in the proximal screw shaft portion. In other words, the outer thread diameter and the thread core diameter show an increase which becomes higher and higher toward the screw head, so that just this proximal thread end located in the area of the entry point cuts into the dense cortical bone material particularly deep and provides for an especially good anchoring.

According to one aspect of the invention, the outer thread diameter increases exponentially and the thread core diameter increases linearly in the proximal screw shaft portion. In other words, the outer thread diameter shows a significantly higher increase as compared to the core diameter, in particular at the proximal thread end which is situated in the area of the entry point, causing a high increase of the thread depth. This allows a good anchoring in the cortical bone shell.

According to one aspect of the invention, the outer thread diameter and the thread core diameter remain constant in a middle screw shaft portion. This geometry satisfies in particular the requirements on a pedicle screw, as the cross-section of the bone is not very large in the area of the pedicle and does not allow large variations in the screw diameter.

According to one aspect of the invention, the thread core diameter increases in a transition area from the middle screw shaft portion to the proximal screw shaft portion, whereas the outer thread diameter remains constant. In other words, the ratio between the outer thread diameter and the thread core diameter first decreases in the transition area before it increases in the proximal screw shaft portion. As the transition area is situated substantially in the area between the entry point and the pedicle, where mainly soft and cancellous bone material and less cortical bone material can be found, the increase of the core diameter allows to exert a radial pressure onto the cancellous bone material and to compact it, without increasing the screw diameter as a whole. Thus, the increase of the outer thread diameter or the diameter ratio can be limited to the last thread turns which are situated in the area of the cortical bone shell, as the sharp thread flanks are necessary in particular for the dense cortical bone material.

According to one aspect of the invention, the outer thread diameter and the thread core diameter decrease toward the screw tip in a distal screw shaft portion. As the thread extends as far as into the screw tip, the screw can be driven into the bone material without a large pre-drilling and without using high pressure.

According to one aspect of the invention, the screw head and the screw shaft are formed as separate parts and can be coupled to each other. This simplifies the manufacturing of the respective individual parts and increases the flexibility and adaptability of the respective components.

According to one aspect of the invention, the screw head may be coupled to a tulip for the fixation of a longitudinal member of a vertebral stabilization system in such manner that the tulip can be pivoted and/or rotated with respect to the longitudinal axis of the screw. Accordingly, the bone screw according to the invention may also be a part of a polyaxial pedicle screw.

BRIEF DESCRIPTION OF THE DRAWINGS

The invention will be described on the basis of several embodiments and comparative examples with reference to the attached drawings in which:

FIG. 2 shows a cross-sectional view of a vertebra including a pedicle screw according to the first embodiment of the invention in the state when screwed in;

DETAILED DESCRIPTION AND COMPARATIVE EXAMPLES

Figure 1A:
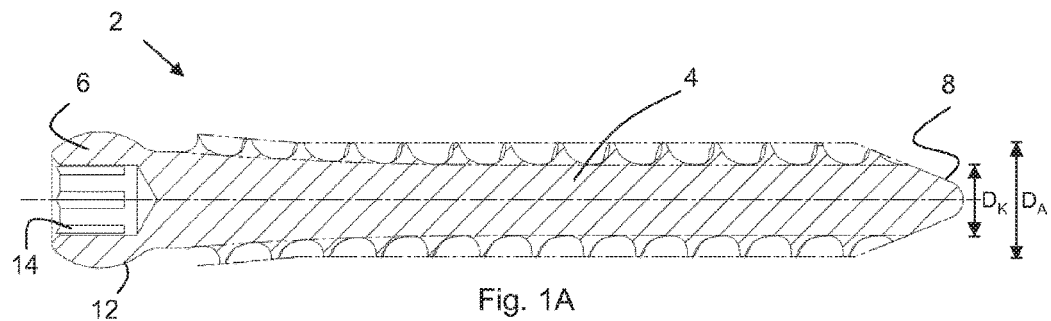
FIGS. 1A and 1B show a pedicle screw according to a first embodiment of the invention in a cross-sectional view and a side view.
Figure 1B:
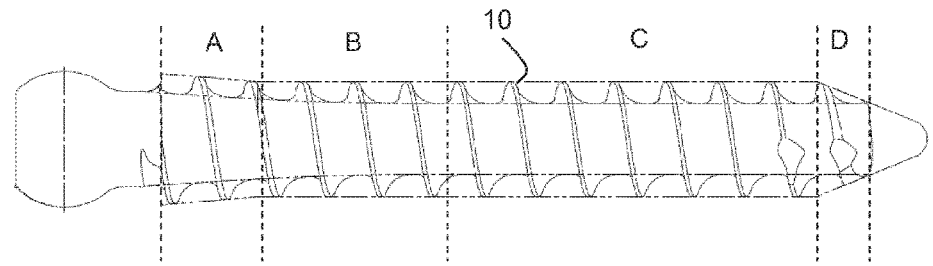

FIGS. 1A and 1B show a bone screw according to the invention, i.e. a pedicle screw 2, in a cross-sectional view and a side view, respectively. The pedicle screw 2 comprises an elongated screw shaft 4 whose proximal end is provided with a screw head 6 and whose distal end conically tapers into a screw tip 8.

The screw shaft 4 is provided with an external thread 10. Here, the illustrated embodiment shows a self-tapping, single-start screw thread. Alternatively, it is also possible to provide a double- or multi-start thread.

The screw head 6, which is formed in one piece with the screw shaft 4, has a spherical surface 12 and an axial recess 14 comprising a hexagon socket or another configuration to be able to drive the pedicle screw 2 into the bone material with a corresponding tool. The screw head 6 and the screw shaft 4, however, may also be realized as a two-piece design.

The ball head shape of the screw head 6 serves for the polyaxial alignment of a so-called tulip with which the pedicle screw 2 cooperates and which serves for receiving and fixing a support via which several pedicle screws can be connected in the framework of a vertebral stabilization system.

In the following, reference will be made in detail to the design of the external thread 10.

Figure 1C:
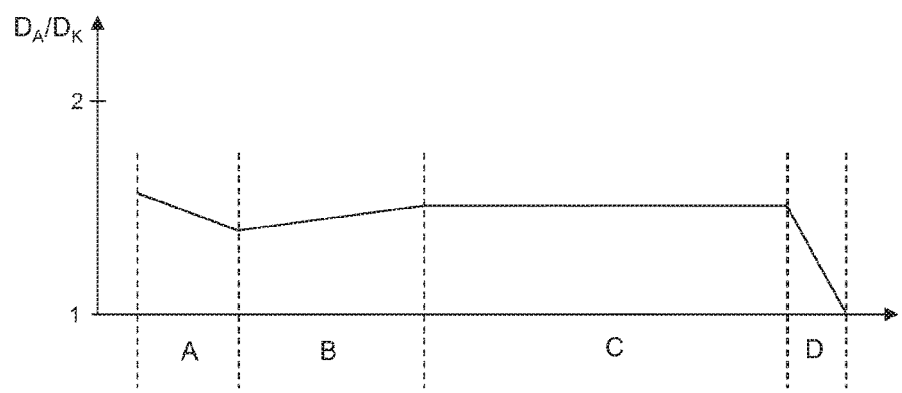
FIG. 1C shows the ratio between the outer thread diameter and the thread core diameter over the length of the thread.

The external thread 10 extends over several screw shaft portions A to D which each have different thread profiles and different ratios of outer thread diameter $D_A$ and thread core diameter $D_K$. These different screw shaft portions A to D are shown, on the one hand, in FIG. 1B and are illustrated on the other hand in the (not true-to-scale) diagram in FIG. 1C.

The screw shaft 4 comprises a relatively long screw shaft portion C in which neither the outer thread diameter $D_A$ nor the thread core diameter $D_K$ change, but remain constant. Provided on the distal side of said shaft portion C having a constant cylindrical thread is the shaft portion D in which the outer thread diameter $D_A$ in the direction toward the screw tip 8 first reduces or peters out to the thread core diameter $D_K$ before the core diameter $D_K$ tapers toward the screw tip 8.

The thread core diameter $D_K$ first increases toward the screw head 6 in a transition area B with an unchanged outer thread diameter $D_A$, whereby the ratio between the outer thread diameter $D_A$ and the thread core diameter $D_K$ decreases in a corresponding manner before the ratio between the outer thread diameter $D_A$ and the thread core diameter $D_K$ again increases in the proximal thread portion or thread's run-out A. To be more precise, both the outer thread diameter $D_A$ and the thread core diameter $D_K$ increase in the area of the thread's run-out A, with the outer thread diameter $D_A$ increasing to a somewhat larger extent.

If the ratio between the outer thread diameter $D_A$ and the thread core diameter $D_K$ increases, this means that the thread becomes deeper and the thread flanks become higher and that the pedicle screw 2 can cut deeper into in the bone material in this zone. On the contrary, if the ratio between the outer thread diameter $D_A$ and the thread core diameter $D_K$ decreases, as is the case in the portions B and D, the thread 10 becomes more shallow and dull as a whole.

In FIGS. 1A and 1B, the envelope curves described by the outer thread diameter and the thread core diameter are indicated by double-dot broken lines. The profile of the outer thread diameter $D_A$ and of the thread core diameter $D_K$ may rise in a curve, e.g. exponentially, as can be seen in FIGS. 1A and 1B. As an alternative to this, the increase of the two diameters $D_A$ and $D_K$ may proceed in linear or conical fashion, or one of them may increase exponentially while the other one may grow in linear manner, as long as it is ensured that the ratio between the outer thread diameter $D_A$ and the thread core diameter $D_K$ has the tendency to increase toward the screw head 6 at least in the thread's run-out zone, i.e. in the screw shaft portion A or in the proximal thread end.

Figure 2:
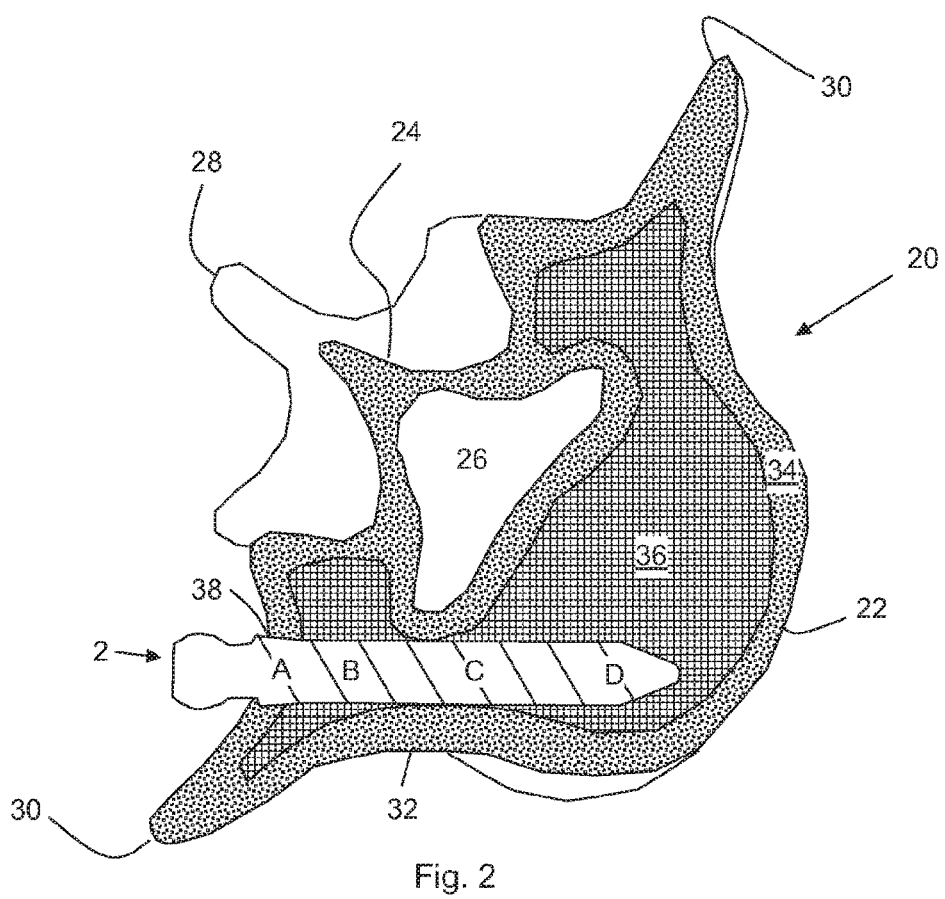

The advantageous effect of the pedicle screw 2 according to the invention is illustrated with the aid of FIG. 2 which shows the pedicle screw 2 in the state when screwed in a vertebra 20. The vertebra 20 comprises a vertebral body 22 and a vertebral arch 24 enclosing a vertebra channel 26. The vertebra 20 further comprises a spinous process 28 and at both sides one transverse process 30 each. The pedicle screw 2 is screwed into the vertebral body 22 between the spinous process 28 and the transverse process 30 via the so-called pedicle 32 and is fixed in the vertebra 20 in this way.

It can be further taken from FIG. 2 that the vertebra 20 has a dense and hard shell made of cortical bone 34 and is composed interiorly, in particular in the area of the vertebral body 22, of a soft and cancellous bone 36. The screw geometry in the area of the middle and distal screw shaft portions is limited substantially by the relatively thin dimensions of the pedicle 32. As the bone constricts in the area of the pedicle, the pedicle 32 predominantly consists of cortical bone material 34.

As can be further seen in FIG. 2, the pedicle screw 2 penetrates different bone layers from an entry point 38 up to the vertebral body 22. In the area of the entry point 38, the vertebra 22 comprises cortical bone material 34, in the area between the entry point 38 and the pedicle 32 it mainly comprises cancellous bone material 36, in the narrowing area of the pedicle 32 it mainly consists of cortical bone material 34 and in the area of the vertebral body 22 it again comprises cancellous bone material 36.

As the pedicle screw 2 has deep and sharp thread flanks in the area of the thread's run-out or screw shaft portion A due to the increasing ratio between outer thread diameter $D_A$ and thread core diameter $D_K$, said flanks are able to cut very well in the cortical bone 34 which is present there and to get anchored therein.

In the transition area B between the thread's run-out A and the middle screw shaft portion C, the pedicle screw 2 has a core diameter $D_K$ which becomes larger toward the screw head 6, so that the cancellous bone material 36 being present between the entry point 38 and the pedicle 32 is compacted by radial pressure by the increasingly larger core diameter $D_K$ during screwing in the pedicle screw 2, whereby the pedicle screw 2 achieves a good grip in the cancellous bone material 36 even in this area.

Since the pedicle screw 2 has a cylindrical thread with an unchanged outer thread diameter $D_A$ thread core diameter $D_K$ in the middle screw shaft portion C, the pedicle screw 2 is also able to cut very well into the cortical bone material 34 of the pedicle 32 and get anchored therein.

Thus, the pedicle screw 2 with its different portions n A, B, C and D having different ratios between outer thread diameter $D_A$ and thread core diameter $D_K$ accounts for the inhomogenous bone strength of a vertebra and in this way provides an improved anchoring in the vertebra 20.

Figure 3A:
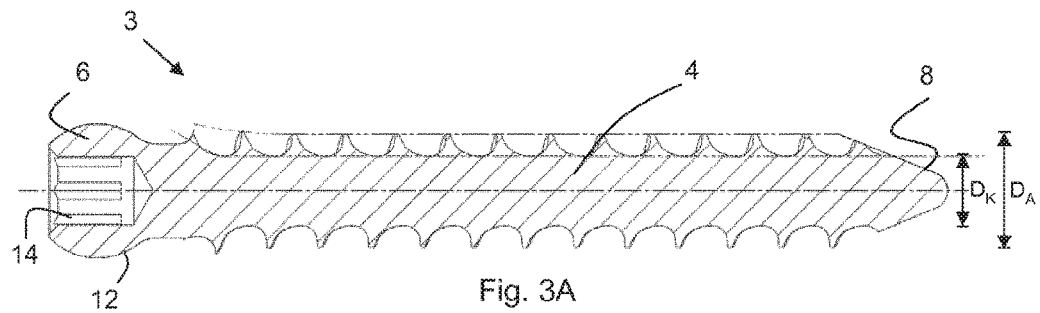
FIGS. 3A and 3B show a pedicle screw according to a second embodiment of the invention in a cross-sectional view and a side view.
Figure 3B:
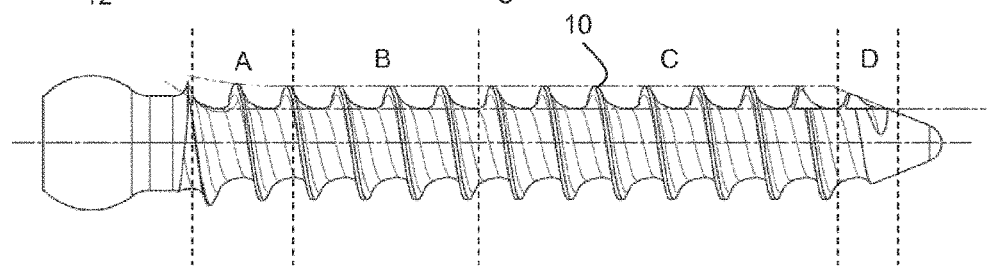

FIGS. 3A and 3B show in a cross-sectional view and a side view a bone screw according to the invention or pedicle screw 3 according to a second embodiment. Similar to the pedicle screw 2 of the first embodiment, the pedicle screw 3 comprises an elongated screw shaft 4 having an external thread 10 whose proximal end is provided with a screw head 6 and whose distal end conically tapers toward a screw tip 8. In the following, only the differences to the first embodiment will be discussed.

Figure 3C:
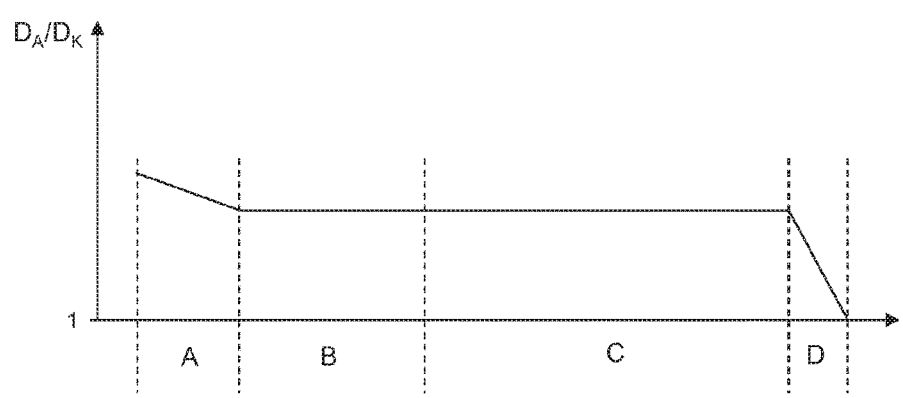
FIG. 3C shows a ratio between the outer thread diameter and the thread core diameter over the thread length.

FIG. 3C shows the (not true-to-scale) ratio between the outer thread diameter $D_A$ and the thread core diameter $D_K$ over the thread length. It can be taken from the diagram of FIG. 3C that the ratio does not change in the transition area B and merely increases in the area of the thread's run-out A. Both the thread core diameter $D_K$ and the outer thread diameter $D_A$ are constant in the screw shaft portions B and C. In the area of the thread's run-out A, the thread core diameter $D_K$ continues to remain constant, whereas the outer thread diameter $D_A$ increases toward the screw head 6, in particular in continuous fashion. This is why the ratio between the outer thread diameter $D_A$ and the thread core diameter $D_K$ increases toward the screw head 6. Consequently, also the pedicle screw 3 according to the second embodiment provides for an equally good anchoring in the cortical bone 34 in the area of the entry point 38.

Whereas in the second embodiment the thread core diameter $D_K$ remains constant and the outer thread diameter $D_A$ increases in the area of the thread's run-out, it is possible according to another (not illustrated) embodiment that the outer thread diameter $D_A$ and the thread core diameter $D_K$ simultaneously increase in the area of the thread's run-out A. In other words, the conical core diameter $D_K$ and the conical external diameter $D_A$ simultaneously extend as far as into the cylindrical diameter portion B. In this case, the outer thread diameter $D_A$ increases to a higher degree than the thread core diameter $D_K$, so that also in this case the ratio between the outer thread diameter $D_A$ and the thread core diameter $D_K$ increases toward the screw head 6 to bring about a good anchoring in the cortical bone 34 in the area of the entry point 38. Consequently, the ratio between the outer thread diameter $D_A$ and the thread core diameter $D_K$ with this embodiment which is not illustrated in the Figures has a qualitatively similar profile than the second embodiment (see FIG. 3C).

For comparison, FIGS. 4, 5, 6 and 7 show the thread profiles of the conventional pedicle screws described at the outset.

Figure 4A:
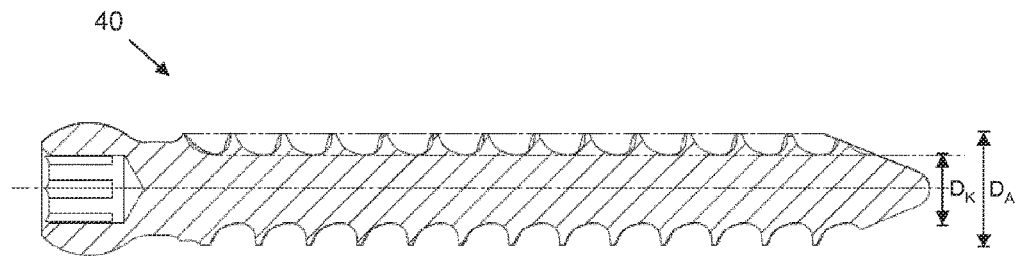
FIGS. 4A and 4B show a conventional pedicle screw comprising a cylindrical thread in a cross-sectional view and a side view.
Figure 4B:
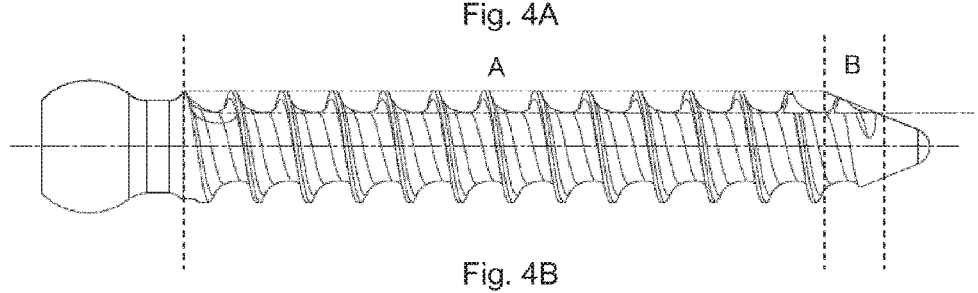
Figure 4C:
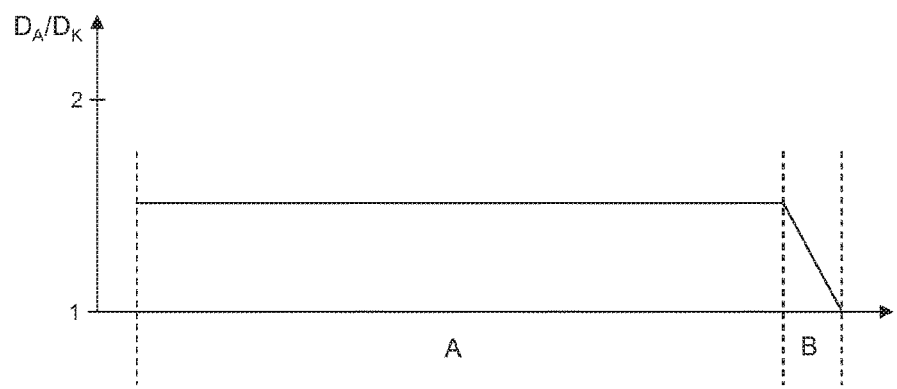
FIG. 4C shows the ratio between the outer thread diameter and the thread core diameter over the thread length.

FIGS. 4A to 4C show a pedicle screw 40 and the corresponding profile of the ratio between the outer thread diameter $D_A$ and the thread core diameter $D_K$ for a cylindrical thread diameter which remains unchanged over the entire shaft length. As is apparent from FIG. 4C, the ratio between the outer thread diameter $D_A$ and the thread core diameter $D_K$ does not change. Such a pedicle screw 40 does not satisfy the different biomechanical properties of the vertebra 20.

Figure 5A:
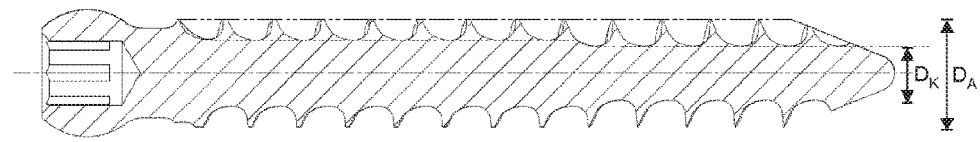
FIGS. 5A and 5B show a conventional pedicle screw comprising a cylindrical thread and a first cylindrical, a conical and a second thread core diameter portion.
Figure 5B:
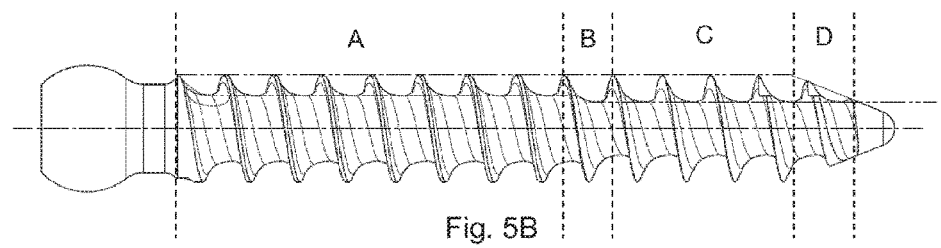
Figure 5C:
FIG. 5C shows the corresponding ratio between the outer thread diameter and the thread core diameter over the thread length.

FIGS. 5A to 5C show corresponding illustrations for a pedicle screw 50 which has a constant outer thread diameter $D_A$ over the entire shaft length, whereas the thread core comprises two cylindrical portions A and C and a conical portion B therebetween. It can be seen in the diagram of FIG. 5C that the ratio between the outer thread diameter and the thread core diameter rather decreases toward the screw head, accompanied by a smaller thread depth.

Figure 6A:
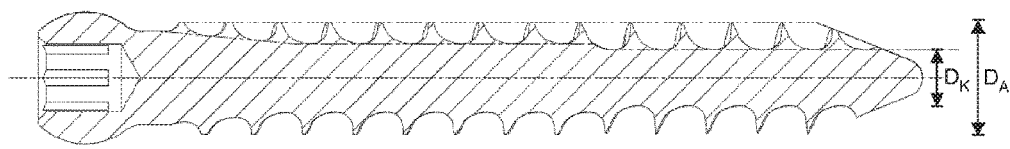
FIGS. 6A and 6B show a conventional pedicle screw comprising a cylindrical thread and a first cylindrical, a first conical, a second cylindrical and a second conical thread core diameter portion.
Figure 6B:
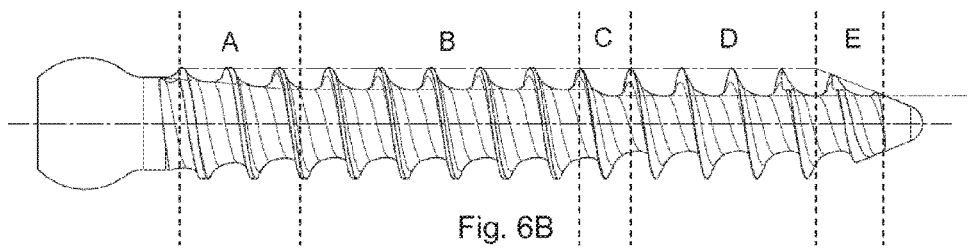
Figure 6C:
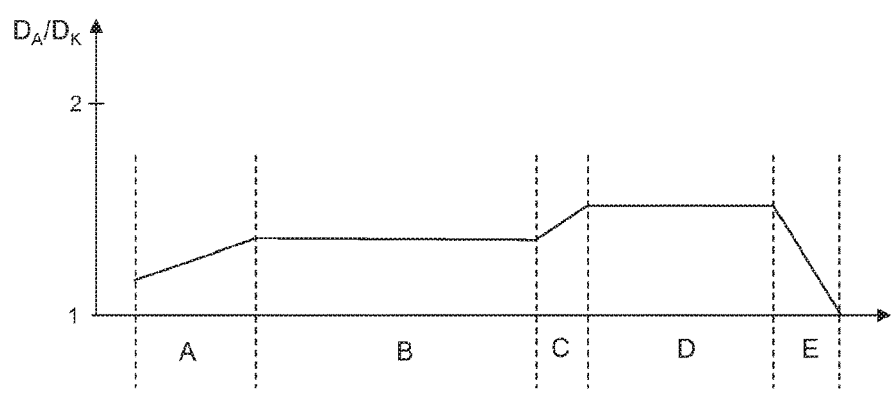
FIG. 6C shows the corresponding ratio between the outer thread diameter and the thread core diameter over the thread length.

The pedicle screw 60 illustrated in FIGS. 6A to 6C differs from the pedicle screw 50 according to FIGS. 5A to 5C in that it comprises—in the area of the thread's run-out A—a further conical thread core diameter portion in which the thread core diameter $D_K$ increases toward the screw head with the outer thread diameter $D_A$ being unchanged, whereby the ratio between the outer thread diameter $D_A$ and the thread core diameter $D_K$ decreases toward the screw head. It can be further seen in the Figures that the screw flanks become more broad and dull in the area of the thread's run-out A, resulting in the disadvantages initially described.

Figure 7A:
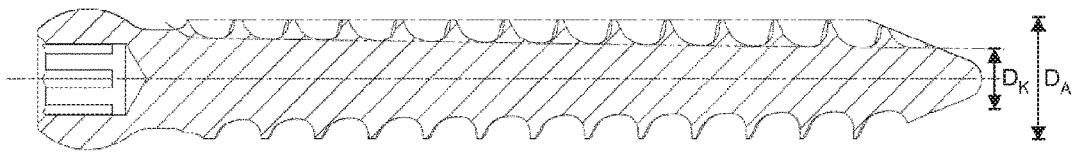
FIGS. 7A and 7B show a conventional pedicle screw comprising a cylindrical outer thread diameter and a conical thread core diameter.
Figure 7B:
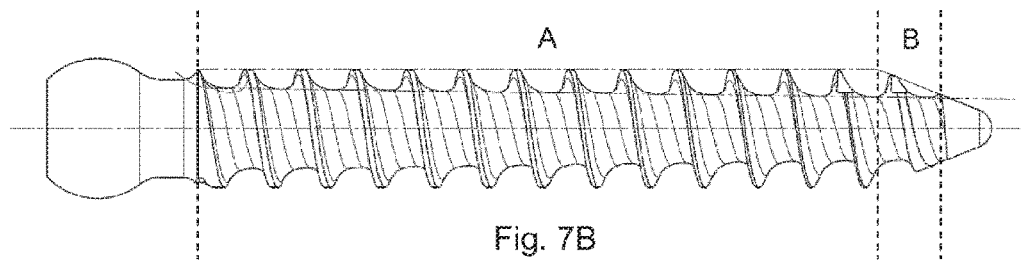
Figure 7C:
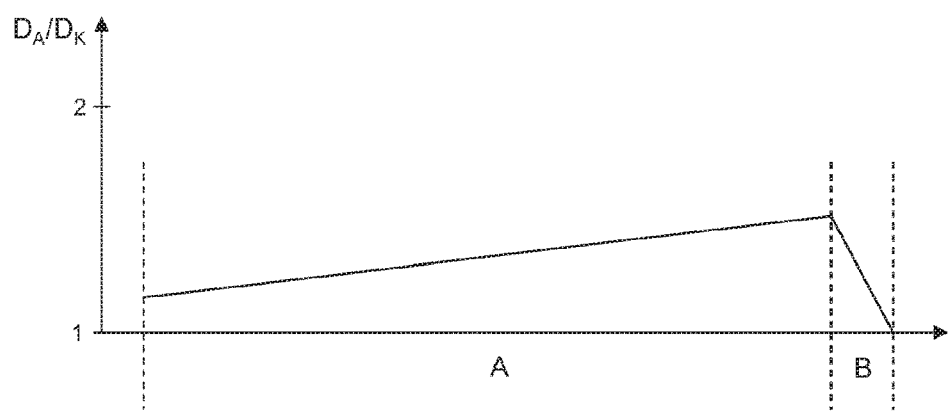
FIG. 7C shows the corresponding ratio between the outer thread diameter and the thread core diameter over the thread length.

FIGS. 7A to 7C show a pedicle screw 70 which has a so-called partially conical thread in which the thread core $D_K$ continuously increases over the shaft length toward the screw head, whereas the outer thread diameter $D_A$ remains constant. Also this pedicle screw is not capable of cutting into the cortical bone material 34 in the area of the entry point 38 and anchoring therein.

The bone screw according to the invention has been illustrated on the basis of a pedicle screw 2, but is not limited thereto. By the enlargement of the ratio between the outer thread diameter $D_A$ and the thread core diameter $D_K$ in the area of the thread's run-out A and the associated deepening of the thread and the improved anchoring in the cortical shell 34 of a bone, the thread design according to the invention can also be utilized with bone screws used for other purposes.

The invention claimed is:

1. A bone screw comprising:
    a screw shaft provided with an external thread and serving for anchoring the bone screw in a bone, the screw shaft comprising an outer thread diameter and a thread core diameter; and
    a screw head provided on a proximal end of the screw shaft,
    wherein, in a proximal screw shaft portion, a ratio between the outer thread diameter and the thread core diameter increases toward the screw head in an area of the external thread's run-out; and
    wherein, in a transition screw shaft portion directly adjacent to the proximal screw shaft portion, the ratio between the outer thread diameter and the thread core diameter decreases toward the screw head, said ratio between the outer thread diameter and the thread core diameter decreasing all the way to where the transition screw shaft portion intersects the proximal screw shaft portion.

2. The bone screw according to claim 1, wherein, in the proximal screw shaft portion, both the outer thread diameter and the thread core diameter increase toward the screw head, with the outer thread diameter increasing to a proportionally higher degree than the thread core diameter.

3. The bone screw according to claim 1, wherein, in the proximal screw shaft portion, the outer thread diameter and the thread core diameter increase toward the screw head in a linear manner or exponential manner.

4. The bone screw according to claim 1, wherein, in the proximal screw shaft portion, the outer thread diameter increases exponentially toward the screw head, and the thread core diameter increases linearly toward the screw head.

5. The bone screw according to claim 1, wherein, in a middle screw shaft portion, the outer thread diameter and the thread core diameter remain constant.

6. The bone screw according to claim 1, wherein, in the transition screw shaft portion, the thread core diameter increases toward the screw head and the outer thread diameter remains constant.

* * * * *